United States Patent [19]

Schöllkopf et al.

[11] Patent Number: 4,925,854
[45] Date of Patent: May 15, 1990

[54] BENZIMIDAZOLE DERIVATIVES

[75] Inventors: Klaus Schöllkopf; Helmut Wachtel, both of Berlin, Fed. Rep. of Germany

[73] Assignee: Schering Aktiengesellschaft, Berlin and Bergkamen, Fed. Rep. of Germany

[21] Appl. No.: 236,383

[22] Filed: Aug. 25, 1988

[30] Foreign Application Priority Data

Aug. 25, 1987 [DE] Fed. Rep. of Germany ....... 3728695

[51] Int. Cl.$^5$ .................. C07D 235/04; A61K 31/415
[52] U.S. Cl. .................................... 514/338; 514/365; 514/387; 546/271; 548/181; 548/305
[58] Field of Search ................ 546/271; 548/305, 181, 548/325, 327; 514/338, 387, 365

[56] References Cited

U.S. PATENT DOCUMENTS

| | | | |
|---|---|---|---|
| 3,813,409 | 5/1974 | Haugwitz | 548/305 |
| 4,367,337 | 1/1983 | Sullivan | 548/305 |
| 4,377,695 | 3/1983 | Lautenschläger et al. | 548/305 |
| 4,554,287 | 11/1985 | Stringer et al. | 548/305 |

Primary Examiner—Mary C. Lee
Assistant Examiner—Catherine S. Kilby Scalzo
Attorney, Agent, or Firm—Millen, White & Zelano

[57] ABSTRACT

Benzimidazole derivatives of general Formula I

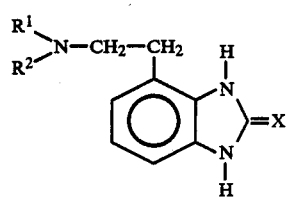

wherein $R^1$ and $R^2$, being identical or different, each mean hydrogen or an optionally substituted hydrocarbon residue and X is oxygen or sulfur, as well as the acid addition salts thereof, are useful, e.g., as dopaminergic agents.

6 Claims, No Drawings

BENZIMIDAZOLE DERIVATIVES

BACKGROUND OF THE INVENTION

The invention relates to novel benzimidazole derivatives, their preparation and their use as medicinal agents.

Many benzimidazoles can influence dopaminergic and adrenergic processes, with the possibility of the occurrence of effects on the central nervous system as well as peripheral effects (PCT/DE 85/00275).

SUMMARY OF THE INVENTION

An object of this invention is to provide novel benzimidazole derivatives, a process for their preparation and a method for using the compounds as medicinal agents.

Upon further study of the specification and appended claims, further objects and advantages of this invention will become apparent to those skilled in the The compounds of this invention have the general

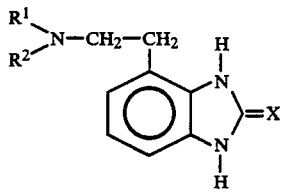

I wherein $R_1$ and $R_2$, being identical or different, each mean hydrogen or an optionally substituted hydrocarbon residue and X is oxygen or sulfur, as well as the acid addition salts thereof.

The compounds of general Formula I also encompass the possible tautomeric forms.

Suitable hydrocarbon residues $R_1$ and $R_2$ are, e.g., saturated aliphatic groups, such as straight-chain and branched lower alkyl residues of up to 6 carbon atoms, and cycloalkyl and cycloalkylalkyl groups of 3–6 carbon atoms.

The following non-limiting examples are cited, for example: methyl, ethyl, propyl, isopropyl, butyl, isobutyl, tert-butyl, sec-butyl, pentyl, hexyl, 2-methyl-butyl, 2,2 dimethylpropyl, cyclopropyl, cyclobutyl, cyclopentyl, cyclohexyl, cyclopropylmethyl, cyclopropylethyl, cyclopentylmethyl, and others.

The alkyl residue can be substituted at any desired location by optionally substituted aromatics or heteroaromatic groups, e.g., typically 1–2 such groups.

When the alkyl substituent is substituted with an aromatic group, it is preferred that $R_1$ and/or $R_2$ are $C_{1-2}$-alkyl. Thus, if the alkyl residue is substituted with an aromatic group, then the Ar-$C_{1-2}$-alkyl residue, such as the benzyl and phenethyl residue, is to be considered preferred.

This aromatic ring can optionally be mono- or poly-substituted, e.g., 1–3 substituents, e.g., $C_{1-4}$-alkyl, $C_{1-4}$-alkoxy, hydroxy, or halogen, especially chlorine or fluorine, but also including bromine and iodine. When there are three substituents, then at least one of the substituents is alkoxy. If the substituent is a heteroaromatic group, then preferred are heteroaromatic rings of 5 or 6 ring atoms which can contain one to two hetero atoms, such as sulfur, oxygen and/or nitrogen, as they are cited below, are suitable, for example: thiophene, furan, pyrrole, pyridine, thiazole, imidazole, pyrazole.

Suitable salts of the compounds of this invention according to Formula I are acid addition salts and are derived from conventionally employed inorganic and organic acids. Examples of such acids include hydrochloric acid, hydrobromic acid, sulfuric acid, citric acid, maleic acid, or fumaric acid.

It was found surprisingly that the compounds of this invention exhibit, in very low doses, a higher dopaminergic effect than levodopa or bromocriptine while simultaneously reducing undesirable side effects.

Based on their profile of effectiveness, the compounds of the present invention are suitable for the treatment of diseases of the central nervous system affected by dopaminergically active agents, such as, for example, Parkinson's disease, acromegaly, and hyperprolactinemia, as well as for the treatment of cardiovascular diseases, e.g., hypertonia, cardiac insufficiency, angina pectoris, and circulatory disturbances, especially for increasing renal blood flow.

The dosage of the compounds according to this invention generally is 0.005 to 50 mg/kg/day, preferably 0.05 to 5.0 when administered to patients to treat Parkinson's disease analogously to the known agent bromocriptine; and is 0.001 to 10 mg/kg/day, preferably 0.01 to 1 when administered to patients to treat acromegaly analogously to the known agent bromocriptine; and is 0.0005 to 5 mg/kg/day, preferably 0.005 to 0.5 when administered to patients, to treat hyperprolactinemia, analogously to the known agent bromocriptine.

The activity of each compound can be determined using conventional protocols, e.g., for Parkinson's disease, see, e.g., Kelly, P.H. Drug-induced motor behavior. Handbook of Psychopharmacology (Iversen L.L.; Iversen S.O. and Snyder S.H.; eds.) Vol. 8, Plenum Press, New York and London, pp. 295–331 (1977).

The special medicinal agents are produced (in dependence on the intended type of administration: orally, parenterally, intravenously, etc.) in the usual way by converting the active compounds with suitable additives, excipients, and flavoring agents into the desired forms of administration, such as tablets, dragees, capsules, solutions, injection solutions, etc.

The compounds of general Formula I are prepared in accordance with methods known per se, for example by cyclizing the compounds of general Formula II

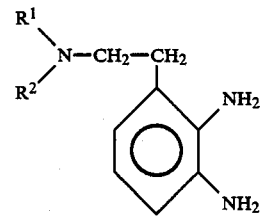

II wherein $R_1$ and $R_2$ have the meanings given above, with a carbonic acid or thiocarbonic acid derivative and optionally thereafter forming the acid addition salt.

Examples of suitable carbonic acid derivatives are phosgene, urea, carbonyldiimidazole, and carbonic acid esters. Examples of suitable thiocarbonic acid derivatives are thiophosgene, thiourea, thiocarbonyldiimidazole, and thiocarbonic acid esters of general Formula III $R^4R^5C=X$, wherein X is oxygen or sulfur and R⁴, R⁵ individually mean chlorine, $NH_2$, imidazolyl or $C_{1-4}$-alkoxy.

Cyclization is carried out at an elevated temperature up to the boiling temperature of the solvent and is generally finished after about 3 hours.

Suitable solvents are inert solvents, such as hydrocarbons, cyclic and acyclic ethers, or aliphatic lower alcohols, such as, for example, toluene, benzene, xylene, tetrahydrofuran, dioxane, methanol, ethanol and propanol.

In order to form salts, the compounds of general Formula I can be dissolved, for example, in alcohol or methylene chloride and combined with a concentrated solution of the desired acid in alcohol at room temperature.

The preparation of the starting compounds is conventional or takes place according to known methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

PREPARATION OF THE STARTING COMPOUNDS

N-[2-(2,3-Diaminophenyl)ethyl]-N,N-dipropylamine (a) For two hours, 5.5 g of 2,3-dinitrotoluene is heated with 13.0 g of bisdipropylamino-tert-butoxymethane to 60° C. After cooling, the reaction mixture is freed of volatile components under a high vacuum, thus obtaining 7.6 g of β-dipropylamino-2,3-dinitrostyrene as an oil.

(b) 7.6 g of the compound obtained in (a) is dissolved in a mixture of 80 ml of methanol, 55 ml of tetrahydrofuran and 11 ml of glacial acetic acid and cooled to −20° C. To this solution is added 2.1 g of sodium cyanoborohydride in incremental portions. Then the mixture is further stirred for two hours at 20° C. Thereafter 45 ml of 2N hydrochloric acid is added to the solution and the latter is stirred for one hour. The reaction mixture is thereupon concentrated and taken up in sodium bicarbonate solution. The aqueous phase is repeatedly extracted with diethylether. The ether phase is separated, dried with sodium sulfate, and combined with oxalic acid. The precipiate is filtered off and rinsed with diethyl ether. Subsequently the base is liberated with sodium bicarbonate solution and extracted with diethyl ether. After removal of the solvent, 1.5 g of N-[2 -(2,3-dinitrophenyl)ethyl]-N,N-dipopylamine is obtained as an oil.

(c) 0.35 g of the compounds produced in (b) is dissolved in 40 ml of methanol and hydrogenated after adding 0.05 g of palladium on carbon. After hydrogen absorption has ceased, the catalyst is filtered off and the filtrate is concentrated, yielding 0.3 g of N-[2 -(23-diaminophenyl)ethyl]-N,N-dipropylamine as an oil.

N- 2 - 2,3 Diaminophenyl)ethyl]-N-(2 -phenylethyl)-N-propylamine (a) For four hours, 9.1 g of 2,3-dinitrotoluene is heated to 70° C. with 15.0 g of bis-dimethylamino-tert-butoxymethane [Chem. Ber. 101 : 41 (1968)]. After cooling, the reaction mixture is freed of volatile components under a high vacuum, thus obtaining 10.1 g of 8-dimethylamino-2,3-dinitrostyrene as an oil.

(b) 10.1 g of the compound obtained in (a) is dissolved in a mixture of 250 ml of water and 100 ml of methanol. To this solution is added 14.0 g of hydroxylamine O-sulfonic acid under agitation. After twelve hours, the reaction mixture is concentrated and extracted repeatedly with dichloromethane. The organic phase is dried over sodium sulfate and filtered off. After concentration, the residue is recrystallized from ethanol, yielding 5.4 g of 2,3-dinitrophenylacetonitrile, mp 88°–90° C..

(c) 5.4 g of the compound obtained in (b) is heated in 30 ml of 60% strength sulfuric acid for four hours to 100° C. After cooling and filtration, 4.9 g of 2,3-dinitrophenylacetic acid is obtained, mp 209°–215° C.

(d) At 0° C., a solution of 2.8 g of the compound obtained in (c) and 2.0 g of N-propylphenethylamine [J. Am. Chem. Soc. 75 : 4664 (1953)] in 50 ml of dichloromethane is combined with 2.6 g of N,N'-dicyclohexylcarbodiimide, dissolved in 30 ml of dichloromethane. After five hours of agitation at 20° C., the mixture is filtered off. The solution is washed with 2N hydrochloric acid, 2N sodium hydroxide solution, and water. After drying over sodium sulfate, the product is filtered off and concentrated, yielding 3.5 g of N-phenyl-ethyl-N-propyl-(2,3-dinitrophenyl)acetamide as an oil.

(e) 3.4 g of the compound produced in (d) is dissolved in 40 ml of tetrahydrofuran. At 0° C., 13 ml of a 1-molar borane solution in tetrahydrofuran is added dropwise under agitation. At 20° C., the mixture is further stirred for twelve hours, then hydrolyzed with water and thereafter with concentrated hydrochloric acid. The reaction mixture is concentrated and neutralized with sodium carbonate solution, then extracted with ethyl acetate. The organic phase is dried over sodium sulfate, filtered off, and concentrated, yielding 2.3 g of N-[2 -(2,3-dinitrophenyl)ethyl]-N-(2 -phenylethyl)-N-propylamine as an oil.

(f) 1.5 g of the compound obtained in (e) is dissolved in 100 ml of methanol and hydrogenated after adding 0.2 g of palaldium on carbon. After hydrogen absorption has ceased, the catalyst is filtered off and the filtrate is concentrated, thus obtaining 1.1 g of N-[2 -(2,3-diaminophenyl)ethyl]-N-(2 -phenylethyl)-N-propylamine as an oil.

N-[2 -(2,3-Diaminophenyl)ethyl]-N-methyl-N-butylamine (a) 9.0 g of 2,1,3-benzothiadiazole-4 -acetic acid [Zhurnal Obshchei Khimii 34 : 1272 (1964)] is dissolved in 100 ml of dichloromethane and combined with 16.8 ml of thionyl chloride. The mixture is heated under reflux for five hours and, after cooling, the volatile components are removed under vacuum. The residue is taken up in 50 ml of dichloromethane and added dropwise under ice cooling to a solution of 10.5 ml of N-methylbutylamine in 50 ml of dichloromethane. After one hour, the reaction mixture is poured on water and the organic phase washed with 1N hydrochloric acid and 1N sodium hydroxide solution. The organic phase is dried over sodium sulfate and, after concentration, the residue is distilled at 0.025 mbar and 170° C., yielding 11.2 g of N-butyl-N-methyl-2,1,3-benzothiadiazole-4-acetamide as an oil.

(b) 11.2 g of the compound obtained in (a) is dissolved in 100 ml of tetrahydrofuran. This solution is added dropwise under ice cooling under a nitrogen atmosphere to 170 ml of a 1-molar borane solution in tetrahydrofuran. The reaction mixture is stirred further for twenty hours at 20° C. Then the mixture is gently combined with 100 ml of 63% strength hydrobromic acid. The mixture is further stirred for four hours and exhaustively concentrated under vacuum. The residue is taken up in water and extracted with dichloromethane. The organic phase is separated and concentrated. The residue is recrystallized from acetone, thus obtaining 6.3 g of 4-[2-(N-butyl-N-methylamino)ethyl]-2,1,3-benzothiadiazole hydrobromide, mp 130° C.

(c) 2.0 g of the compound obtained in (b) is suspended in 30 ml of tetrahydrofuran. Under cooling, 0.7 g of lithium aluminum hydride is added. After two hours, the batch is poured on sodium bicarbonate solution and extracted with diethyl ether. The organic phase is dried over sodium sulfate and concentrated, yielding 1.3 g of N-[2-(2,3-diaminophenyl)ethyl]-N-methyl-N-butylamine.

The following compounds are produced analogously:
N-[2-(2,3-diaminophenyl)ethyl]-N-[2-(2-thienyl)ethyl]-N-propylamine
N-[2-(2,3-diaminophenyl)ethyl]-N-[2-(3-thienyl)ethyl]-N-propylamine.

EXAMPLE 1

4-[2-(N-Butyl-N-methylamino)ethyl]-2,3-dihydro-2-benzimidazolethione, Hydrobromide 650 mg of N-[2-(2,3-diaminophenyl)ethyl]-N-methyl-N-butylamine and 600 mg of N,N'-thiocarbonyldiimidazole are dissolved in 30 ml of tetrahydrofuran and heated under reflux for three hours. After cooling, the mixture is extensively concentrated. The residue is taken up in water and extracted with ethyl acetate. The organic phase is dried over sodium sulfate and concentrated. The residue is taken up in ethanol and combined with 33% strength hydrobromic acid. After renewed concentration, the residue is recrystallized from isopropanol, thus obtaining 370 mg of 4-[2-(N-butyl-N-methylamino)ethyl]-2,3-dihydro-2-benzimidazolethione, hydrobromide, mp 264°–266° C.

EXAMPLE 2

4-[2-[N-(2-Phenylethyl)-N-propylamino]ethyl]-2,3-dihydro-2-benzimidazolethione, Hydrobromide In accordance with the procedure described in Example 1, 370 mg of N-[2-(2,3-diaminophenyl)ethyl]-N(2-phenylethyl)-N-propylamine and 230 mg of N,N'-thiocarbonyldiimidazole yield 170 mg of 4-[2-[N-(2-phenylethyl)-N-propylamino]ethyl]-2,3-dihydro-2-benzimidazolethione, hydrobromide, mp 198°–201° C.

EXAMPLE 3

4-[2-[N-Propyl-N-[2-(2-thienyl)ethylamino]]ethyl]-2,3-dihydro-2-benzimidazolone, Fumarate 1.40 g of N-[2-(2,3-diaminophenyl)ethyl]-N[2-(2-thienyl)ethyl]-N-propylamine and 0.70 g of N,N'-carbonyldiimidazole is dissolved in 50 ml of tetrahydrofuran and heated under reflux for three hours. After cooling, the mixture is extensively concentrated. The residue is taken up in water and extracted with ethyl acetate. The organic phase is dried over sodium sulfate and concentrated. The residue is taken up in ethanol and combined with fumaric acid. After renewed concentration, the residue is recrystallized from isopropanol, thus obtaining 0.55 g of 4-[2-[N-propyl-N-[2-(2-thienyl)ethylamino]]ethyl]-2,3-dihydro-2-benzimidazolone, fumarate, mp 170°–173° C.

EXAMPLE 4

4-[2-(N,N-Dipropylamino)ethyl]-2,3-dihydro-2-benzimidazolethione, Hydrobromide 360 mg of N-[2-(2,3-diaminophenyl)ethyl]-N,N-dipropylamine is heated under reflux for three hours with 30 ml of tetrahydrofuran and 360 mg of N,N'-thiocarbonyldiimidazole. After concentration, the residue is combined with water and methanol. The precipitate is dissolved in ethanol and converted into the hydrobromide with hydrobromic acid. Yield: 120 mg of 4-[2-(N,N-dipropylamino)ethyl]-2,3-dihydro-2-benzimidazolethione, hydrobromide, mp 250°–255° C.

EXAMPLE 5

4-[2-(N,N-Dipropylamino)ethyl]-2,3-dihydro-2-benzimidazolone, Hydrobromide 360 mg of N-[2-(2,3-diaminophenyl)ethyl]-N,N-dipropylamine is heated with 30 ml of tetrahydrofuran and 300 mg of N,N'-carbonyldiimidazole for three hours under reflux. After concentration, the residue is taken up in aqueous alcohol and combined with hydrobromic acid. After renewed concentration, the residue is recrystallized from isopropanol/diethyl ether, thus obtaining 90 mg of 4-[2-(N,N-dipropylamino)ethyl]-2,3-dihydro-2-benzimidazolone, hydrobromide, mp 189°–192° C.

EXAMPLE 6

4-[2-(N-Butyl-N-methylamino)ethyl]-2,3-dihydro-2 benzimidazolone, Hydrobromide

In accordance with the procedure disclosed in Example 1, 400 mg of N-[2-(2,3-diaminophenyl)ethyl]-N-methyl-N-butylamine and 350 mg of N,N'-carbonyldiimidazole yield 185 mg of 4-[2-(N-butyl-N-methylamino)ethyl]-2,3-dihydro-2-benzimidazolone, hydrobromide, mp 240°–242° C.

EXAMPLE 7

4-[2-[N-(2-Phenylethyl)-N-propylamino]ethyl]-2,3-dihydro-2-benzimidazolone,Fumarate According to the process set forth in Example 3, 250 mg of N-[2-(2,3-diaminophenyl)ethyl]-N-(2-phenylethyl)-N-propylamine and 250 mg of N,N'-carbonyldiimidazole yield 147 mg of 4-[2-[N-(2-phenylethyl)-N-propylamino]ethyl]-2,3-dihydro-2-benzimidazolone, fumarate, mp 176°–177° C.

EXAMPLE 8

4-[2-[N-Propyl-N-[2-(2-thienyl)ethylamino]]ethyl]-2,3-dihydro-2-benzimidazolethione, Hydrobromide In accordance with the process disclosed in Example 1, 450 mg of N-[2-(2,3-diaminophenyl)ethyl]-N[2-(2-thienyl)ethyl]-N-propylamine and 400 mg of N,N'-thiocarbonyldiimidazole yield 260 mg of 4-[2-[N-propyl-N[2-(2-thienyl)ethylamino]]ethyl]-2,3-dihydro-2-benzimidazolethione, hydrobromide, mp 193°–195° C.

EXAMPLE 9

4-[2-[N-Propyl-N-[2-(3-thienyl)ethylamino]]ethyl]-2,3-dihydro-2-benzimidazolone, Fumarate In accordance with the procedure set forth in Example 3, 450 mg of N-[2-(2,3-diaminophenyl)ethyl]-N[2-(3-thienyl)ethyl]-N-propylamine and 230 mg of N,N'-carbonyldiimidazole yield 173 mg of 4-[2-[N-propyl-N[2-(3-thienyl)ethylamino]]ethyl]-2,3-dihydro-2-benzimidazolone, fumarate, mp 114°–117° C.

EXAMPLE 10

4-[2-[N-Propyl-N-[2-(3-thienyl)ethylamino]]ethyl]-2,3-dihydro-2-benzimidazolethione, Fumarate In accordance with the process disclosed in Example 3, 900 mg of N-[2-(2,3-diaminophenyl)ethyl]-N[2-(3-thienyl)ethyl]-N-propylamine and 500 mg of N,N'-thiocarbonyldiimidazole yield 455 mg of 4-[2-[N-propyl-N-[2-(3-thienyl)ethylamino]]ethyl]-2,3-dihydro-2-benzimidazolethione, fumarate, mp 207°–209° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzimidazole of the formula:

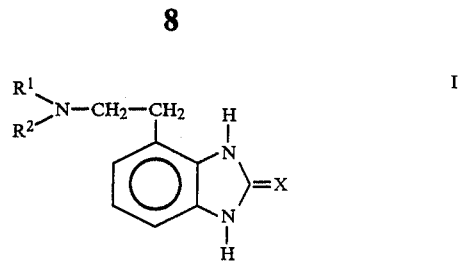

wherein
R$^1$ and R$^2$ are identical or different and each is hydrogen or a saturated aliphatic group, wherein said aliphatic group is a lower alkyl group having 1–6 carbon atoms, cycloalkyl of 3–6 carbon atoms or cycloalkylalkyl of 3–6 carbon atoms wherein said lower alkyl groups may be substituted with a phenyl, thiophene, furan, pyrrole, pyridine, thiazole, imidazole or pyrazole group, and wherein said phenyl group may be substituted by lower alkyl, lower alkoxy, hydroxy or halogen; and
is oxygen or sulfur, or a pharmacologically acceptable acid addition salt thereof.

2. 4-[2-(N,N-Dipropylamino)ethyl]-2,3-dihydro-2-benzimidazolethione, 4-[2-(N,N-dipropylamino)ethyl]-2,3-dihydro-2-benzimidazolone, 4-[2-(N-butyl-N-methylamino)ethyl]-2,3-dihydro-2-benzimidazolone, 4-[2-[N-(2-phenylethyl)-N-propylamino]ethyl]-2,3-dihydro-2-benzimidazolone, 4-[2-[N-propyl-N-[2-(2-thienyl)ethylamino[ethyl[[-2,3-dihydro-2-benzimidazolethione, 4-[2-(N-butyl-N-methylamino)ethyl]-2,3-dihydro-2-benzimidazolethione, 4-[2-[N-(2-phenylethyl)-N-propylamino]ethyl]-2,3-dihydro-2-benzimidazolethione, 4-[2-[N-propyl-N-[2-(2-thienyl)ethylamino]]ethyl]-2,3-dihydro-2-benzimidazolone, 4-[2-[N-propyl-N-[2-(3-thienyl)ethylamino]]ethyl]-2,3-dihydro-2-benzimidazolone, 4-[2-[N-propyl-N-[2-(3-thienyl)ethylamino]]ethyl]-2,3-dihydro-2-benzimidazolethione, each a compound of claim 1.

3. A benzimidazole derivative of claim 1, wherein at least one of R$^1$ and R$^2$ is C$_{1-6}$-alkyl.

4. A benzimidazole derivative of claim 3, wherein alkyl is substituted.

5. A pharmaceutical composition comprising an effective amount of a compound of claim 1 and a pharmaceutically acceptable carrier.

6. A pharmaceutical composition comprising an effective amount of a compound of claim 2 and a pharmaceutically effective carrier.

* * * * *

UNITED STATES PATENT AND TRADEMARK OFFICE
CERTIFICATE OF CORRECTION

PATENT NO. : 4,925,854

DATED : May 15, 1990

INVENTOR(S) : KLAUS SCHOLLKOPF ET AL

It is certified that error appears in the above-identified patent and that said Letters Patent is hereby corrected as shown below:

Column 8, claim 1, line 22:

reads "is oxygen or sulfur, or a pharmacologically accept-"

Should read -- X is oxygen or sulfur, or a pharmacologically accept- --

Signed and Sealed this

Seventh Day of May, 1991

Attest:

HARRY F. MANBECK, JR.

Attesting Officer     Commissioner of Patents and Trademarks